(12) United States Patent
Bodjanski et al.

(10) Patent No.: US 9,934,592 B1
(45) Date of Patent: Apr. 3, 2018

(54) METHOD AND SYSTEM FOR DETERMINING A 6-DOF-POSE OF AN OBJECT IN SPACE

(71) Applicant: CARL ZEISS INDUSTRIELLE MESSTECHNIK GMBH, Oberkochen (DE)

(72) Inventors: Mariusz Bodjanski, Zielonka (PL); Maciej Kraszewski, Slupsk (PL); Arkadiusz Smigielski, Kobylnica (PL)

(73) Assignee: CARL ZEISS INDUSTRIELLE MESSTECHNIK GMBH, Oberkochen (DE)

( * ) Notice: Subject to any disclaimer, the term of this patent is extended or adjusted under 35 U.S.C. 154(b) by 0 days.

(21) Appl. No.: 15/351,679

(22) Filed: Nov. 15, 2016

(51) Int. Cl.
*G06T 7/70* (2017.01)
*G06T 7/20* (2017.01)
(Continued)

(52) U.S. Cl.
CPC .............. *G06T 7/70* (2017.01); *G06T 7/13* (2017.01); *G06T 7/20* (2013.01); *G06T 7/60* (2013.01);
(Continued)

(58) Field of Classification Search
CPC .... G06T 7/20; G06T 7/73; G06T 7/13; G06T 7/60; G06T 2200/04; G06T 2207/30204; G06T 2219/2016; G06T 17/00; G06T 19/00; G06T 7/292; G06T 7/70; A61B 2034/107; A61B 2034/101; A61B 2034/2055; A61B 2090/3937; A61B 2034/2068; A61B 2034/305; A61B 2090/365; A61B 2090/3966; A61B 5/1127; A61B 6/547; A61B 2034/2046; A61B 2034/2057; A61B 2090/3945
See application file for complete search history.

(56) References Cited

U.S. PATENT DOCUMENTS 5,751,843 A * 5/1998 Maggioni ................ G06T 7/20
                                                                  382/154
6,724,930 B1 * 4/2004 Kosaka ................ G01B 11/002
                                                                  382/154
(Continued)

FOREIGN PATENT DOCUMENTS

WO    WO 2016/0071227 A1    5/2016

OTHER PUBLICATIONS

Bradley et al., Oct. 2004, "Tracking a sphere with six degrees of freedom". pp. 1-24.*
(Continued)

*Primary Examiner* — Manav Seth
(74) *Attorney, Agent, or Firm* — Harness, Dickey & Pierce, P.L.C.

(57) ABSTRACT

A method and a system for determining a 6-DOF-pose of an object in space use an optical-tracking marker attached to the object. The marker comprises an inner marker area having a circular contour with a known radius and a marker pattern defining at least one characteristic marker feature. A camera image of the marker typically shows an elliptical representation of the circular contour and the marker pattern. Based on the image, parameters describing the elliptical representation are determined and the 6-DOF-pose of the marker in space is derived using the parameters.

19 Claims, 6 Drawing Sheets

(51) Int. Cl.
*G06T 7/73* (2017.01)
*G06T 7/13* (2017.01)
*G06T 7/60* (2017.01)
*G06T 17/00* (2006.01)
*A61B 34/20* (2016.01)
*A61B 90/00* (2016.01)

(52) U.S. Cl.
CPC ............... *G06T 7/73* (2017.01); *G06T 17/00* (2013.01); *A61B 2034/2046* (2016.02); *A61B 2034/2055* (2016.02); *A61B 2090/3937* (2016.02); *G06T 2200/04* (2013.01); *G06T 2207/30204* (2013.01)

(56) References Cited

U.S. PATENT DOCUMENTS

| | | | | |
|---|---|---|---|---|
| 6,792,370 B2* | 9/2004 | Satoh | .......................... | G06T 7/80 345/419 |
| 7,231,063 B2* | 6/2007 | Naimark | .............. | G06K 9/4609 348/169 |
| 7,242,460 B2* | 7/2007 | Hsu | ...................... | G06K 9/3241 356/4.01 |
| 7,257,237 B1* | 8/2007 | Luck | ..................... | A61B 5/1113 382/103 |
| 7,698,094 B2* | 4/2010 | Aratani | ................... | G01S 5/163 356/614 |
| 7,881,767 B2* | 2/2011 | Strommer | ............ | A61B 5/0555 600/407 |
| 8,422,777 B2* | 4/2013 | Aller | .................... | G06K 9/3216 382/165 |
| 8,948,471 B2* | 2/2015 | Fichtinger | .............. | A61B 6/504 382/128 |
| 9,002,062 B2* | 4/2015 | Aller | .................... | G06K 9/3216 382/103 |
| 9,135,513 B2* | 9/2015 | Takemoto | ................ | G06K 9/32 |
| 9,292,755 B2* | 3/2016 | Aller | ................... | G06K 9/3216 |
| 2008/0262345 A1* | 10/2008 | Fichtinger | .............. | A61B 6/504 600/426 |
| 2015/0125033 A1* | 5/2015 | Murphy | .................. | G06T 7/251 382/103 |
| 2017/0278237 A1* | 9/2017 | Lovberg | ................. | G06T 7/248 |

OTHER PUBLICATIONS

Jiang et al., 2002, "A simulation study of the degrees of freedom of movement in reaching and grasping". pp. 881-904.*
Lilian Calvet et al.; Detection and Accurate Localization of Circular Fiducials under Highly Challenging Conditions; 2016; pp. 562-570.

* cited by examiner

METHOD AND SYSTEM FOR DETERMINING A 6-DOF-POSE OF AN OBJECT IN SPACE

BACKGROUND OF THE INVENTION

The present invention relates to a method and a system for determining a 6-DOF-pose of an object in space. More particularly, the invention relates to a method and a system which employ one or more 2D optical-tracking markers having defined features. At least one such optical-tracking marker is attached to the object and at least one image of the optical-tracking marker is captured while the at least one optical-tracking marker is attached to the object. Using image processing technologies, 3D-position and 3D-orientation of the optical-tracking marker in space and, consequently, 3D-position and 3D-orientation of the object in space can be determined.

Determining both 3D-position and 3D-orientation of an object in space requires determining at least 6 parameters which represent 6 degrees of freedom (DOF), namely 3 parameters representing the 3D position along the three axes of a 3D coordinate system and 3 further parameters representing angular orientation about any of the three axes. Typically, the 3D coordinate system is defined relative to the at least one camera by using appropriate calibration. The 6-Degree-of-Freedom-(DOF) pose comprises both the 3D position and the 3D orientation relative to the coordinate system.

International patent application WO 2016/071227 A1, which is also assigned to the assignee of the present invention, discusses some prior art and a new approach for determining 3D position and orientation of an object in space using optical-tracking markers. According to the prior art, the optical-tracking markers often have a black-and-white chessboard pattern (checkered flag pattern), and the centroid of the marker is typically defined by an intersection of straight edges or lines formed between alternating bright and dark regions of the pattern. Typically, the centroid of the checkered pattern marker is estimated as a position of the marker within the 2D-image captured by the camera. For determining a 6-DOF-pose of an object, a plurality of markers and/or a plurality of cameras for capturing various marker images are required.

WO 2016/071227, in contrast, proposes optical-tracking markers having a substantially continuous or "analog" pattern comprising greyscale values or color-values which vary in accordance with a non-binary multitone characteristic along a circular path around the marker centroid. Image analysis of such marker patterns allows for improved accuracy. In addition, a plurality of markers can be individually coded and distinguished from one another by using different analog marker patterns. The approach of WO 2016/071227 has already proved to be successful, but there is still room for further improvement. In particular, it is desirable to further improve the accuracy in the determination of the 3D-position and 3D-orientation of an object bearing the marker. In addition, it is desirable to achieve 6-DOF-pose determination with a minimum number of markers and cameras in order to enable savings in costs and space.

A conference paper titled "Detection and Accurate Localization of Circular Fiducials under Highly Challenging Conditions" by Lilian Calvet, Pierre Gurdjos, Carsten Griwodz, Simone Gasparini from The IEEE Conference on Computer Vision and Pattern Recognition (CVPR), 2016, pp. 562-570, proposes optical-tracking markers (termed as fiducials) having a plurality of circular, concentric black-and-white rings. In one academic example, a circular marker having a single ring painted with a continuous gradation of greyscale values is examined. Paths in the marker imager are created such that the directions of path segments are given by image gradients.

The known methods and systems still leave room for improvement, especially with respect to accuracy, detection speed and costs of implementation.

SUMMARY OF THE INVENTION

Against this background, it is an object of the present invention to provide an improved method and an improved system for determining a 6-DOF-pose of an object in space with high accuracy.

It is another object to provide an improved method and an improved system for determining a 6-DOF-pose of an object in space in a cost-effective manner. In particular, it is an object to provide a method and a system for determining a 6-DOF-pose of an object in space with a minimum of cameras and a minimum of optical-tracking markers.

It is yet another object to provide a method and a system for detecting, identifying and tracking an object in space using 2D optical-tracking markers in a fast and convenient manner.

Favorable applications of the new method and system may be in the fields of industrial metrology, industrial manufacturing, computer-assisted surgery and others.

In view of the above, there is provided a method for determining a 6-DOF-pose of an object in space, the method comprising the steps of attaching a 2D optical-tracking marker to the object, said 2D optical-tracking marker comprising an inner marker area having a circular contour with a known radius and having a marker pattern defining at least one characteristic marker feature; providing a camera and a coordinate system relative to the camera; capturing an image of said 2D optical-tracking marker attached to the object by using the camera, said image comprising an elliptical representation of said circular contour as a result of a generally non-orthogonal viewing angle of said camera relative to said marker area, said elliptical representation having a semi-major axis, a semi-minor axis, an ellipse center point and an ellipse orientation relative to the coordinate system; determining, based on the image, a first parameter representing the semi-major axis, determining a second parameter representing the semi-minor axis, determining a third parameter and a forth parameter together representing the ellipse center point, and determining a fifth parameter representing the ellipse orientation; identifying an image representation of said at least one characteristic marker feature in the image; determining a correspondence between said image representation and the at least one characteristic marker feature; determining a 6-DOF-pose of the 2D optical-tracking marker in space based on the first parameter, the second parameter, the third parameter, the fourth parameter, the fifth parameter and the correspondence; and determining the 6-DOF-pose of the object based on the 6-DOF-pose of the 2D optical-tracking marker.

There is also provided a system for determining a 6-DOF-pose of an object in space, the system comprising a 2D optical-tracking marker configured to be attached to the object, said 2D optical-tracking marker comprising an inner marker area having a circular contour with a known radius and having a marker pattern defining at least one characteristic marker feature, comprising a camera, and comprising a processing unit configured for executing steps of defining a coordinate system relative to the camera; capturing an image of said 2D optical-tracking marker attached to the object by using the camera, said image comprising an elliptical representation of said circular contour as a result of a generally non-orthogonal viewing angle of said camera relative to said marker area, said elliptical representation having a semi-major axis, a semi-minor axis, an ellipse center point and an ellipse orientation relative to the coordinate system, based on the image; determining a first parameter representing the semi-major axis, determining a second parameter representing the semi-minor axis, determining a third parameter and a forth parameter together representing the ellipse center point, and determining a fifth parameter representing the ellipse orientation; identifying an image representation of said at least one characteristic marker feature in the image; determining a correspondence between said image representation and the at least one characteristic marker feature; determining a 6-DOF-pose of the 2D optical-tracking marker in space based on the first parameter, the second parameter, the third parameter, the fourth parameter, the fifth parameter and the correspondence; and determining the 6-DOF-pose of the object based on the 6-DOF-pose of the 2D optical-tracking marker.

Advantageously, the new method is implemented using a camera and a processing unit, which may be a general purpose computer or a special purpose computer, where an appropriate computer program is stored and executed, said computer program being designed and configured for determining the 6-DOF-pose of the 2D optical-tracking marker in accordance with the afore-mentioned method.

The new method and the new system employ a 2D optical-tracking marker which is attached to the object. The optical-tracking marker has a circular contour with a known radius and a marker pattern with at least one characteristic marker feature. An image of said optical-tracking marker is captured by means of the camera while the optical-tracking marker is attached to the object. Accordingly, an image of at least a part of the object to which the optical-tracking marker is attached is captured. For small objects, the image may contain the whole object together with the tracking marker. For large objects, it might be sufficient to capture an image of that part of the object where one or more optical-tracking markers are attached.

As will be explained in further detail below, some exemplary embodiments of the new method and system employ a single optical-tracking marker, i.e. only one optical-tracking marker, attached to the object, and only one image from one camera is processed at a time for determining a current 6-DOF-pose. Other exemplary embodiments may use a plurality of markers attached to one object and/or a plurality of images taken substantially simultaneously by a plurality of cameras. In the latter case, each camera has an individual line of sight relative to the marker, which results in different images from different camera perspectives. Moreover, if a plurality of markers are attached to one object, each marker is shown in a different position and orientation in each one of the one or more images. While some embodiments do not require a plurality of images nor a plurality of markers, a plurality of images and/or a plurality of markers provide for a higher amount of image information which can advantageously be used for even further increasing accuracy and/or reliability of the new method and system.

While many prior art systems and methods try to find one point of an optical-tracking marker, such as the marker center point, for determining the marker position in space, the new method and system are based on the idea of determining a correspondence between the circular contour of the marker and a generally elliptical representation of this circular contour in the camera image. In other words, the new method and system make beneficial use of a correspondence between a 2D-characteristic of the marker and the corresponding 2D-representation in the camera image, while many prior art systems and methods only exploit a 1D correspondence between a singular point of the marker and its corresponding representation in the camera image. Determining and exploiting a correspondence between 2D-characteristics of the marker and the marker image allow for higher accuracy and for a space and cost saving implementation using only one marker and one camera.

In a preferred refinement of the invention, the circular contour defines a circle center point, and the marker pattern comprises an intensity profile that varies substantially continuously along a circular path around the circle center point. Preferably, the circular path around the circle center point is concentrically with respect to the circular contour of the marker.

A marker with such a marker pattern distinguishes from almost any markers proposed in the prior art. While prior art markers typically have binary patterns, such as a checkered flag pattern, the marker pattern according to this refinement has a substantially analog nature. "Substantially analog" means in this context that the marker pattern includes multiple different intensity values which are perceived as analog or at least almost analog by the human eye from a certain distance. In some embodiments, the marker pattern includes at least $2^5=32$ different intensity values. The skilled person will acknowledge, however, that digital printing technologies may create some sort of a small step profile along the circular path, which is not truly analog in a strict sense. In any case, the marker pattern is a multitone pattern and therefore carries a high amount of information, which is advantageous both for individually coding a plurality of similar markers and for achieving high accuracy in determining the 6-DOF-pose of the marker. The variation of the intensity profile along a circular path around the circle center point is advantageous for determining a correspondence between the marker and its representation in the camera image.

In a further refinement, the intensity profile is constant along any radial path starting at the circle center point and extending radially outward from the circle center point a defined distance.

This refinement is advantageous, because it facilitates image analysis and allows for higher accuracy in an efficient manner. In some exemplary embodiments, the intensity profile is constant along any radial path starting at the circle center point and extending radially outward up to a pre-defined radius, which is smaller than the known radius of the circular contour. In these exemplary embodiments, the marker pattern may be divided in subsections forming an inner circle and a number of outer rings. An advantage of these exemplary embodiments is the increased number of codes that can be used for optically differentiating between a plurality of markers.

In a further refinement, the method further comprises a step of sampling a plurality of first image values in the image, a step of determining a plurality of gradient vectors, with each gradient vector representing a direction of maximum change in the intensity profile at the respective first image value, and a step of determining a marker center point based on the plurality of gradient vectors. In the corresponding system, the processing unit is further configured for executing the afore-mentioned steps.

This refinement provides a very efficient approach for determining an image representation of the marker center point. The image representation may advantageously be used either as a relevant ellipse center point or as an information additional to the ellipse center point. It should be observed that the "true" center point of the ellipse in the camera image may be different from the marker center point determined in accordance with this refinement. Determining both the true ellipse center point and the marker center point is advantageous for increasing the accuracy, as will be explained further down below. Taking the marker center point determined in accordance with this refinement as "relevant" ellipse center point is an efficient approach for determining this ellipse parameter. In any case, this refinement is useful not only in the context of the present invention, but also on its own, namely as a method for determining a circular marker center point from its elliptical representation in a camera image.

In another refinement, the circular contour defines a circle center point, and the marker pattern comprises intensity values that vary in accordance with a function that results from a linear combination of a limited number of sinusoidal components along a circular path around the circle center point. Preferably, the limited number of sinusoidal components is less than 10, more preferably less than 5 and even more preferably not higher than 3.

According to this refinement, the marker pattern comprises an intensity profile that can mathematically be described as a sum of a limited number of sinusoidal components. In particular, the intensity pattern can be described by a Fourier series having the limited number of sinusoidal components. This refinement allows for a very efficient determination of the marker pose with a particular high accuracy. In particular, this refinement is advantageous for establishing the at least one characteristic marker feature and for determining the correspondence between said marker feature and its respective image representation.

In another refinement, the marker pattern is a greyscale pattern.

This refinement allows for a very cost-efficient implementation of the new system and method.

In another refinement, the marker pattern comprises at least three different color components.

This refinement helps to increase information density in the marker pattern, which might advantageously be used for differentiating and individually coding a plurality of different markers.

In another refinement, the marker pattern is radially-symmetric.

Radial-symmetry defines a symmetry around a central axis, which is typically orthogonal to the circle center point of the marker in the preferred embodiments. A radially-symmetric pattern facilitates the image analysis and, therefore, the determination of the 6-DOF-pose of the marker in space.

In another refinement, the circular contour defines a circle center point, and the characteristic feature comprises a rotation angle of the marker pattern around the circle center point.

A rotation angle around the circle center point can reliably be detected in the marker image using available image analysis technologies. Therefore, this refinement facilitates a cost-effective implementation of the new method and system and contributes to high accuracy.

In another refinement, the method further comprises a step of sampling a plurality of second image values in the image along an elliptical path around the ellipse center point in order to determine an image pattern, and a step of determining a transfer function representing a relationship between the marker pattern and the image pattern.

This refinement, which can advantageously be used independently and beyond the scope of the present invention in order to determine a correspondence between a circular marker and its elliptical representation, helps to further increase accuracy in the determination of the 6-DOF-pose of the optical-tracking marker. It is particularly advantageous if combined with a marker pattern having an intensity profile that can be described by the sum of a limited number of sinusoidal components. In general, the refinement allows to determine the full 2D-correspondence between the marker pattern and its elliptical representation. In some preferred embodiments, the transfer function is determined by means of a Fourier series approximation. Advantageously, the transfer function describes the perspective distortion of the elliptical marker image relative to the circular marker pattern.

In another refinement, the method further comprises the steps of determining a polar coordinate image from the camera image by means of a coordinate transformation from Cartesian coordinates to polar coordinates using the ellipse center point as polar coordinate origin, low pass filtering of the polar coordinate image in order to determine a de-noised polar coordinate image, and determining a de-noised Cartesian coordinate image from the de-noised polar coordinate image by means of a coordinate transformation from polar coordinates to Cartesian coordinates. The processing unit of the new system is advantageously configured to execute these additional steps in preferred refinements.

This refinement can also advantageously be used independently and beyond the scope of the present invention in connection with any method for de-noising an image showing an elliptical representation of a circular marker or object. The refinement applies low pass filtering, which removes high frequency components in the image, and thereby reduces noise. By applying a coordinate transformation from Cartesian coordinates to polar coordinates using the ellipse center point as a polar coordinate origin in advance, the ellipse center point is substantially kept free from the filtering process. This results in maintaining high accuracy with respect to the image position of the ellipse center point. Accordingly, this refinement contributes to very high accuracy.

In another refinement, the step of determining the 6-DOF-pose of the 2D optical-tracking marker comprises a step of numerically solving a system of equations relating the 6-DOF-pose of the 2D optical-tracking marker in space to the first parameter, the second parameter, the third parameter, the fourth parameter, the fifth parameter and the correspondence.

As already indicated above, the representation of the circular marker contour in the camera image will typically comprise an elliptical contour as a result of an oblique line of sight of the camera onto the marker. In other words, the circular contour of the marker will appear as an ellipse in the camera image. As will be understood by those skilled in the art, the elliptical representation and the circular contour of the marker itself are related and the relationship depends on the relative position and orientation of the marker relative to the camera. Accordingly, determining the relationship makes it possible to determine the 6-DOF-pose of the marker relative to the camera. This refinement allows a very efficient implementation of the new method and system.

In another refinement, precisely one 2D optical-tracking marker is attached to the object and one image of said 2D optical-tracking marker is used in the step of determining the first parameter, the second parameter, the third parameter, the fourth parameter, the fifth parameter and the correspondence.

Using a single optical-tracking marker in combination with a single image allows for a very cost-efficient and rather fast implementation of the new method and system. This is particularly advantageous for tracking 3D movements of an object. On the other hand, exploiting a plurality of 2D optical-tracking markers and/or analyzing a plurality of images captured by a plurality of cameras with different viewing angles enables an even higher accuracy, which can be advantageous in high-end metrological applications or computer-assisted neurosurgery.

Accordingly, a plurality of 2D optical-tracking markers may be attached to the object and one or more images may be processed in other refinements. Preferably, the plurality of 2D optical-tracking markers comprise a first 2D optical-tracking marker having a first marker pattern and comprise a second 2D optical-tracking marker having a second marker pattern, the first and second marker patterns being different from one another.

This refinement facilitates differentiation between first and second markers, thereby increasing processing speed and reliability of the new method and system.

In another refinement, the 2D optical-tracking marker further comprises an outer background area that distinguishes from the inner marker area. Preferably, the elliptical representation of the inner marker area is analyzed using edge detection technologies exploiting the edge between the outer background area and the inner marker area.

This refinement also facilitates an efficient and reliable implementation of the new method and system.

It goes without saying that the features mentioned above and those yet to be explained below cannot only be used in the respective combinations disclosed, but also in different combinations or alone without departing from the scope of the present invention.

BRIEF DESCRIPTION OF THE DRAWINGS

Further features and advantages will be apparent from the following detailed description. Unless otherwise defined, all technical and scientific terms have the meaning as commonly understood by one of ordinary skill in the art. In the drawings.

DESCRIPTION OF PREFERRED EMBODIMENTS

Figure 1:
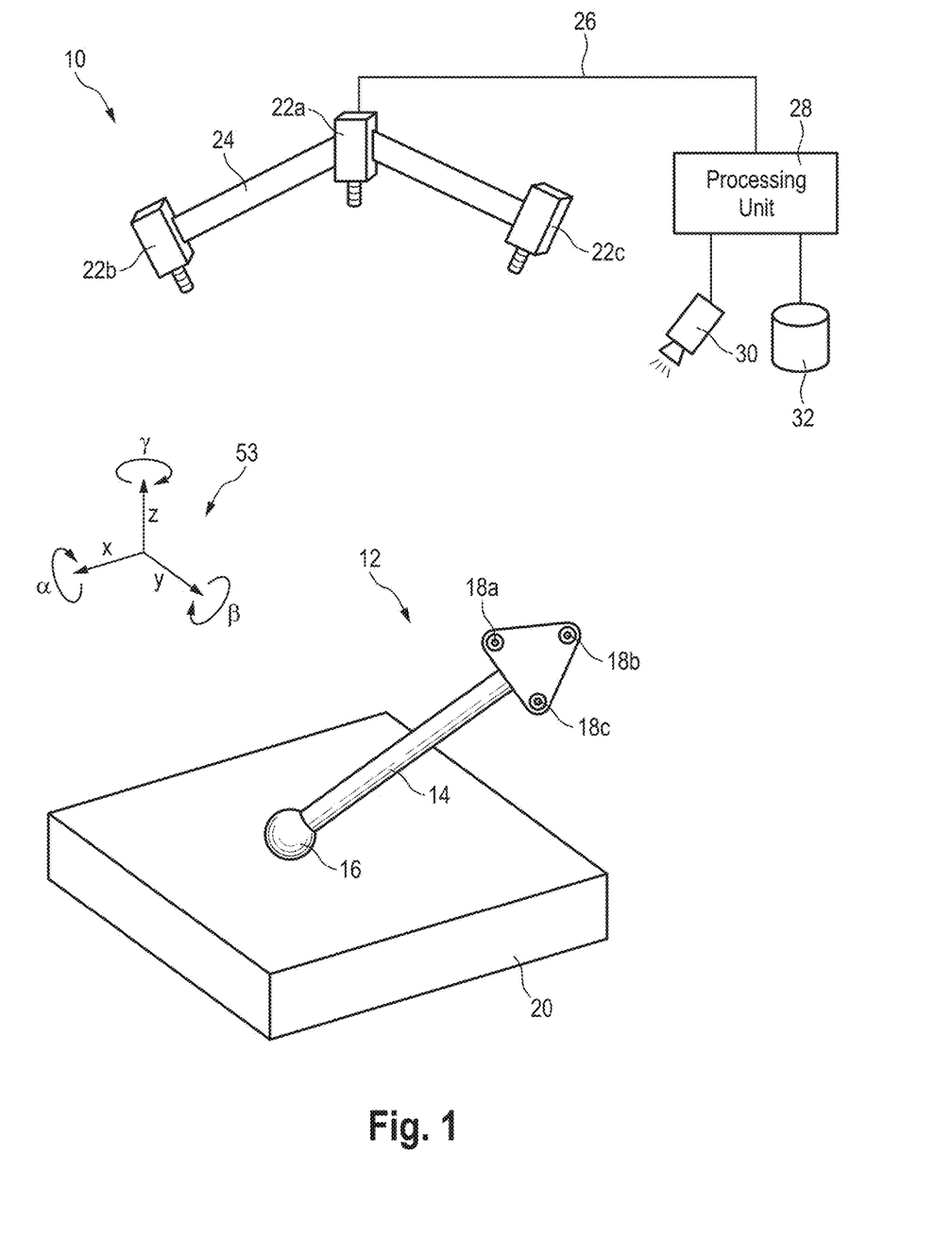
FIG. 1 shows a simplified schematic illustration of an exemplary embodiment of a system implementing the method.

In FIG. 1, an exemplary embodiment of the new system is designated by reference number 10 in its entirety. System 10 is designed and configured for detecting the 6-DOF-pose of a hand-operated tool 12. Accordingly, tool 12 is an object having a 6-DOF-pose in space, which is to be determined by means of system 10. System 10 may implement exemplary embodiments of the new method, as will be explained in the following.

In this exemplary embodiment, tool 12 comprises a handle 14 which can be manually held and operated by a human (not illustrated). A ball 16 is arranged on a distal end of handle 14. At the proximal end, a plate carrying three optical-tracking markers 18a, 18b, 18c is arranged. In this exemplary embodiment, tool 12 is designed and configured for identifying measurement points on a measurement object 20, such as a car body part or any other measurement object. Accordingly, system 10 and tool 12 together may form a hand-operated coordinate measurement device that can advantageously be used in industrial metrology applications.

In this exemplary embodiment, system 10 comprises three cameras 22a, 22b, 22c, which are arranged on a structure 24 in such a manner that at least one of cameras 22a, 22b, 22c has a field of view for taking images of tool 12 with markers 18a, 18b, 18c. while it is used on measurement object 20. Other exemplary embodiments may involve only one camera 22, two cameras or any other suitable number of cameras. The cameras might be configured to capture greyscale images, color images, infrared images or any useful combination thereof. By way of example, camera 22a is shown to be connected to processing unit 28 via line 26. It goes without saying that further cameras 21b, 22c are also connected to processing unit 28, if appropriate. In general, line 26 might be an electrical and/or optical cable. Additionally or as an alternative, one or more cameras 22 might be connected to processing unit 28 in a wireless manner.

Processing unit 28 is configured for controlling cameras 22a, 22b, 22c and for processing image data provided by the cameras. In particular, processing unit 28 is designed and configured for determining the 6-DOF-pose of tool 12 in accordance with embodiments of the method explained further below.

Processing unit 28 may control illumination 30, which might include LED lamps or any other suitable lamps generating light in the visible and/or infrared range. While illumination control by processing unit 28 is advantageous, other exemplary embodiments might be implemented without dedicated illumination control.

Processing unit 28 is connected to or may comprise a non-transitory data memory 32 where a computer program is stored. In some exemplary embodiments, processing unit 28 is a general purpose computer, such as a commercially available personal computer operating under Windows®, Linux or MacOS and the computer program from memory 32 comprises program code designed and configured for implementing embodiments of the new method in combination with at least one marker 18 and at least one camera 22.

Some exemplary embodiments of the new system and method may employ a single optical-tracking marker attached to the object, which is particularly advantageous for small objects having a limited surface area for attaching an appropriate marker. Using two, three or even more tracking markers, however, allows for improved accuracy and might help to detect and track the 6-DOF-pose of an object under circumstances, where parts of the object might be hidden from the camera field of view.

Figure 2:
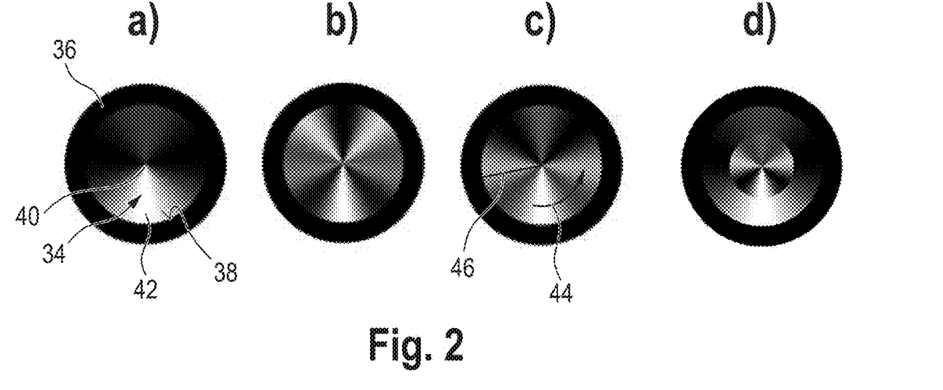
FIG. 2 shows four exemplary embodiments of 2D optical-tracking markers which can advantageously be used in the method and system of FIG. 1.
Figure 3:
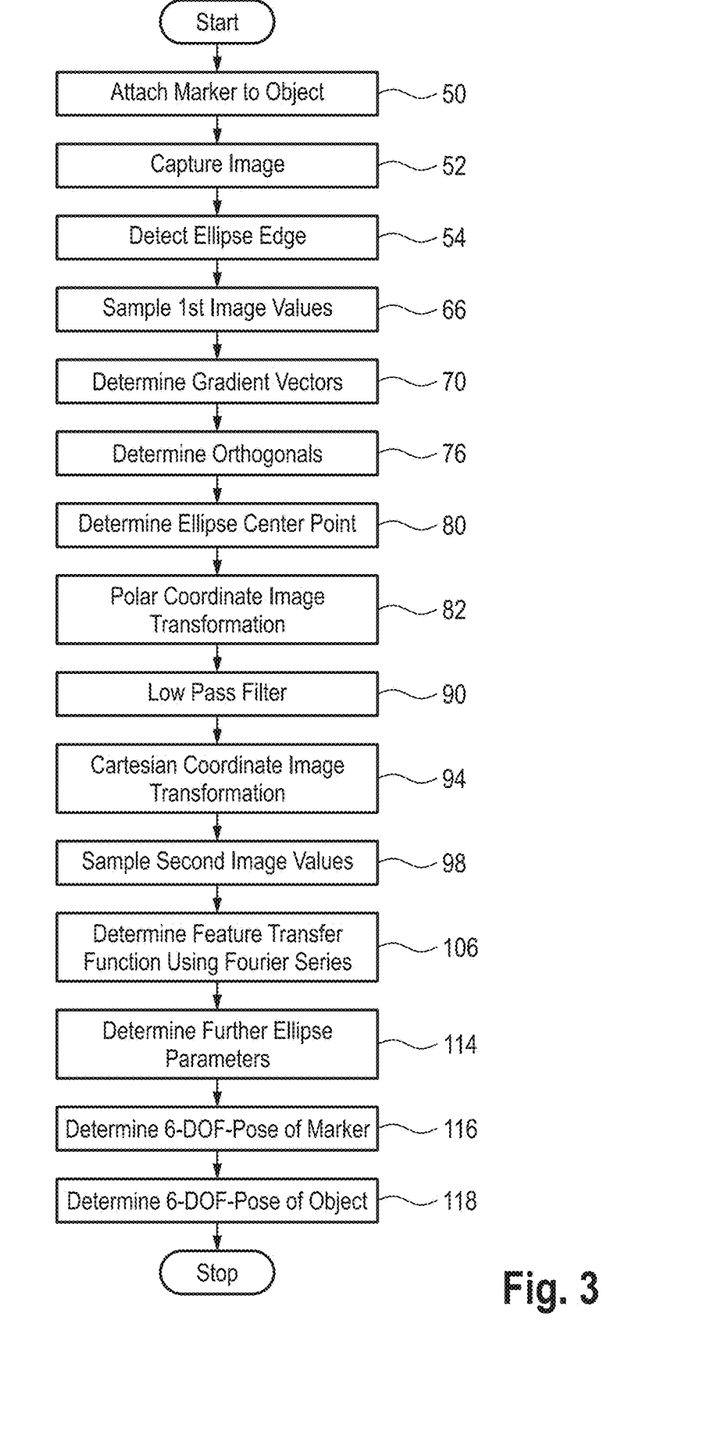
FIG. 3 shows a simplified flow diagram for explaining an exemplary embodiment of the method.

FIG. 2 shows some exemplary embodiments of preferred 2D markers. In the embodiments shown, the markers comprise an inner marker area 34 and an outer background area 36, although other exemplary embodiments might be implemented without outer background area 36. While inner marker area 34 has a circular contour 38 in the exemplary embodiments, outer background area 36 might have a different form. For example, outer background area 36 might be a square, triangle, hexagon or may have any other form. In the preferred embodiments, circular contour 38 has a defined and known radius R (see FIG. 6). Circular contour 38 defines a circle center point 40.

In the preferred embodiments, marker area 34 comprises a marker pattern 42 with an intensity profile that varies substantially continuously along circular path 44 around circle center point 40. Accordingly, marker pattern 42 may be perceived as analog or almost analog, although marker pattern 42 may be produced from a plurality of dots or pixels. In some preferred embodiments, the intensity profile is constant along any radial path 46 starting at the circle center point and extending radially outward (cf. FIG. 2c). As can be seen in FIG. 2d, marker area 34 may comprise a plurality of marker patterns, which are arranged concentrically with respect to each other.

Figure 6:
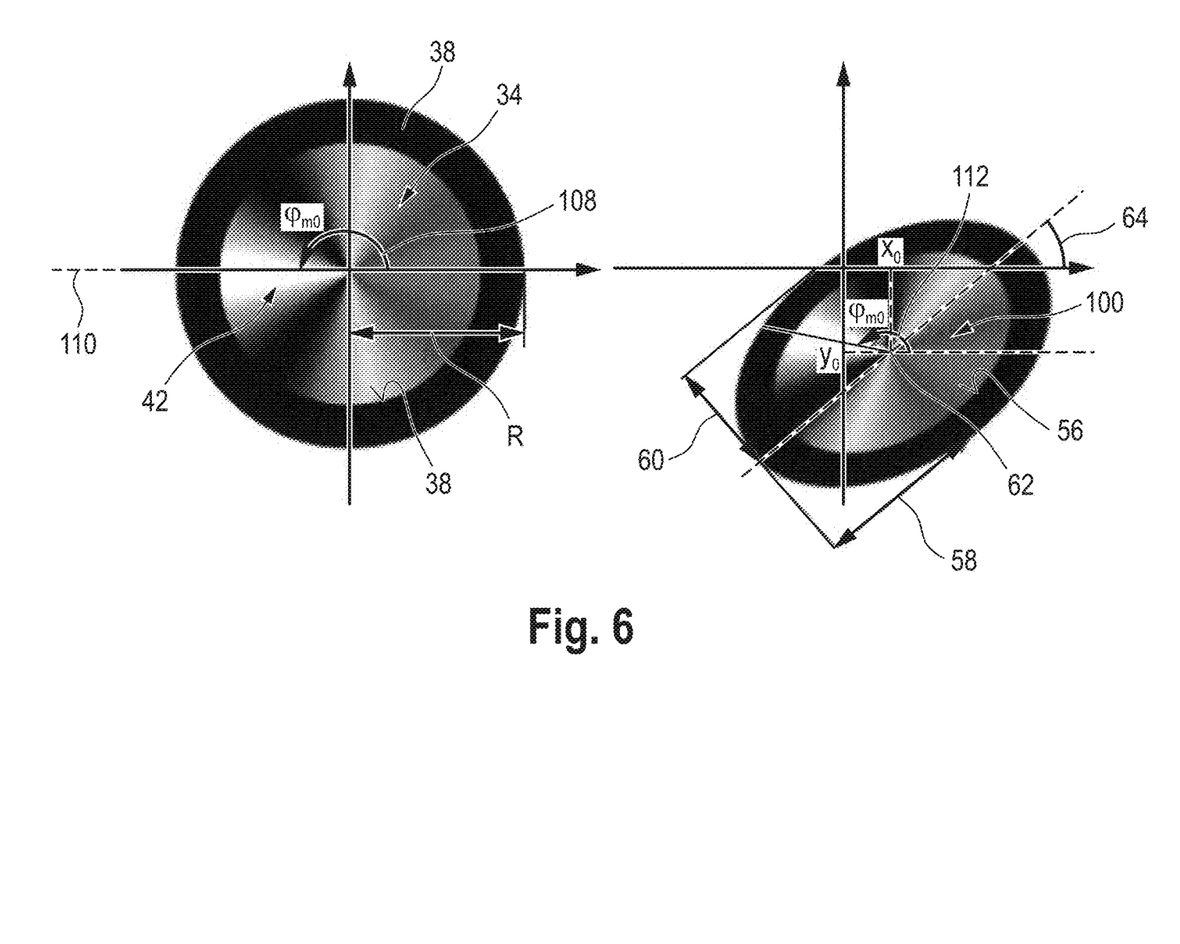
FIG. 6 shows a simplified illustration for explaining advantageous embodiments of the method.

In some preferred embodiments, the intensity profile along circular path 44 varies in accordance with a function that results from a linear combination of a limited number of sinusoidal components. By way of example, FIG. 6 shows a marker with an intensity profile that varies along a circular path 44 in accordance with a function that is shown in FIG. 7a). Different intensity profiles for different markers may be used as individual codes that allow to distinguish the individual markers one from the other in the image analysis processing. Preferably, the number of sinusoidal components is 1, 2 or 3.

In the following, a preferred exemplary embodiment of the new method implemented by means of system 10 is explained. According to step 50, at least one marker is attached to the object, such as markers 18a, 18b, 18c attached to hand-operated tool 12. According to step 52, an image of the at least one marker is captured using at least one of cameras 22a, 22b, 22c, while the at least one marker is attached to the object. The captured image is supplied to processing unit 28 for image analysis and determination of the 6-DOF-pose of the at least one marker in space. The at least one marker may have any position along each of the x,y,z-axes of a coordinate system 53, and it may be rotated about any of the x,y,z-axes by a rotation angle α, β, γ (cf. FIG. 1).

According to step 54, an elliptical representation of circular contour 38 in the image is detected. As the skilled person will readily understand and as is illustrated in FIG. 6, the circular marker contour 38 will typically appear as an ellipse 56 due to the perspective distortion. The elliptical representation or ellipse 56 can be characterized by ellipse parameters, namely a semi-major axis 58, a semi-minor axis 60, an ellipse center point 62 defined by two coordinates $x_e$, $y_e$ in a 2D image-coordinate system, and by an ellipse orientation 64, which can advantageously be defined as an angle between a first axis co-linear with the semi-major axis and a second axis of the image coordinate system. Semi-major axis 58, semi-minor axis 60, the 2D-coordinates of the ellipse center point 62 and ellipse orientation 64 define a first, second, third, fourth and fifth parameter characterizing the elliptical representation of the circular marker in the camera image.

Figure 4:
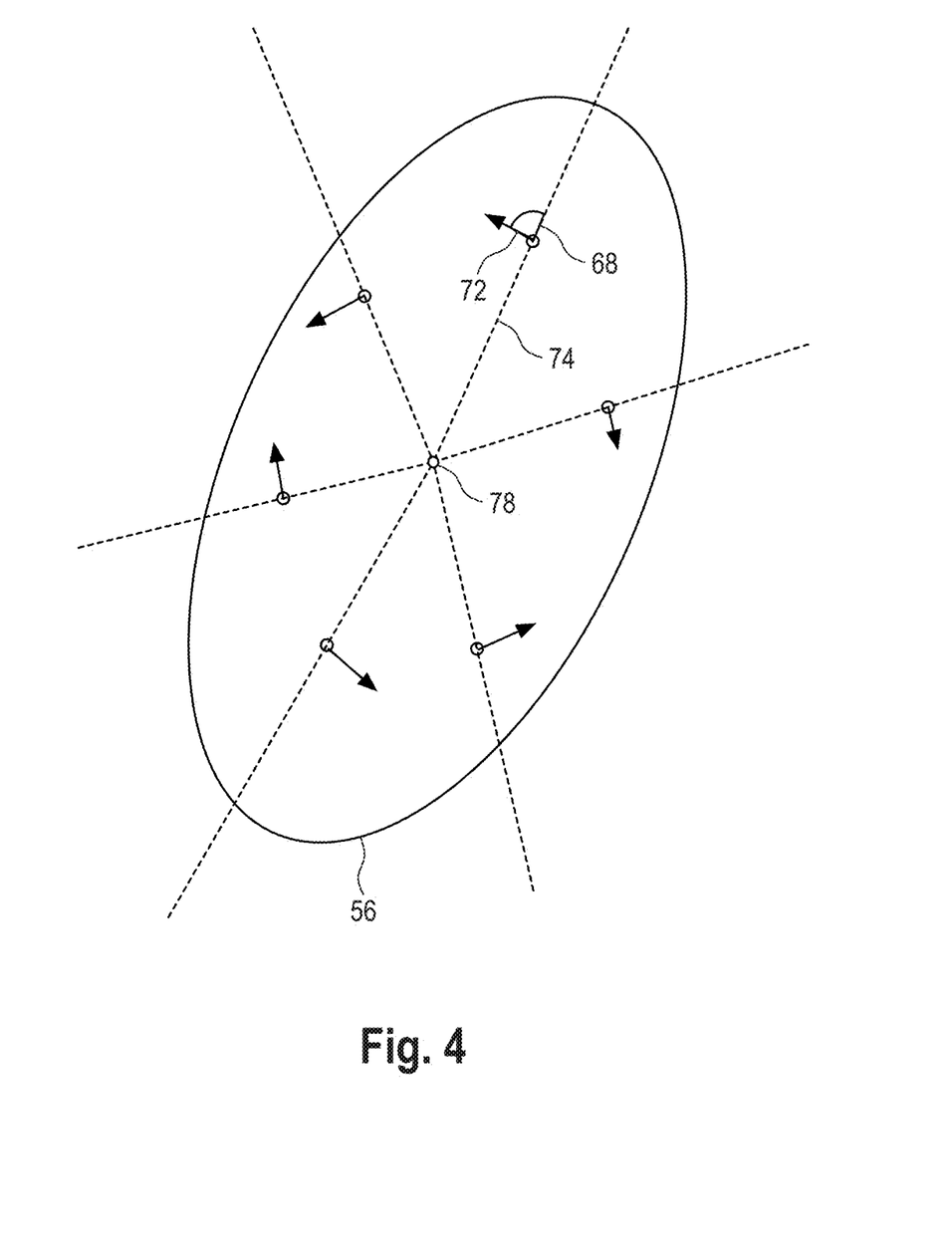
FIG. 4 is a simplified illustration of an elliptical representation of a 2D tracking marker for explaining a preferred exemplary embodiment using gradient vectors.

According to step 66, first image values from the elliptical representation of inner marker area 34 in the camera image are sampled. FIG. 4 shows a simplified illustration of elliptical representation 56 and sampled image values 68.

According to step 70 a gradient vector 72 is determined for each sampled first image value 68. Gradient vector 72 represents a direction of maximum change in the intensity profile at the respective image value 68. In the exemplary embodiments, the intensity profile of inner marker area 34 does not vary along any radial path starting at the circle center point and extending radially outward. Therefore, gradient vector 72 advantageously points in a direction that is orthogonal to a radial line, as it is indicated in FIG. 4. Accordingly, orthogonal straight lines 74 may be determined in step 76 for each of sampled first image values 68, with each orthogonal straight line 74 extending in a radial direction and being orthogonal with respect to one gradient vector 72. The plurality of orthogonal lines 74 define a point of intersection 78, which may be used as a relevant ellipse center point in some preferred embodiments according to step 80. In practice, it might happen that the plurality of orthogonal lines 74 do not converge at one point of intersection 78. Therefore, the relevant ellipse center point may be determined as a point that minimizes the sum of distances to each of orthogonal lines 74.

It should be noted that point of intersection 78 might be slightly dislocated from "true" ellipse center point 62 of ellipse 56. Therefore, point of intersection 78 may be interpreted differently in some preferred embodiments and advantageously be used as an image representation of circular marker center point 40, while "true" ellipse center point 62 is determined as an additional information in order to achieve higher accuracy, as will be explained further down below. Ellipse center point 62 may be determined using conventional image processing techniques. For example, ellipse center point 62 may be determined as point of intersection between semi-major axis 58 and semi-minor axis 60, with these two ellipse axes being detected using image analysis techniques.

The first image values are preferably selected with a sufficient distance from expected point of intersection 78 within inner marker area 34. The image values might be selected in various ways. For example, the image values may be selected such that they surround the expected point of intersection in a substantially uniform manner. Additionally or alternatively, first image values might be selected randomly and/or sample image values might be selectively placed in areas where the intensity profile changes particularly strong.

In some preferred embodiments, orthogonal lines 74 may be weighted in step 80. For example, if a gradient vector corresponding to a respective line 74 is rather weak (which means that the intensity profile does not change very strongly at the selected image value relative to adjacent image values), the respective line 74 might be treated with a smaller weight compared to other orthogonal lines associated with stronger gradient vectors.

Figure 5:
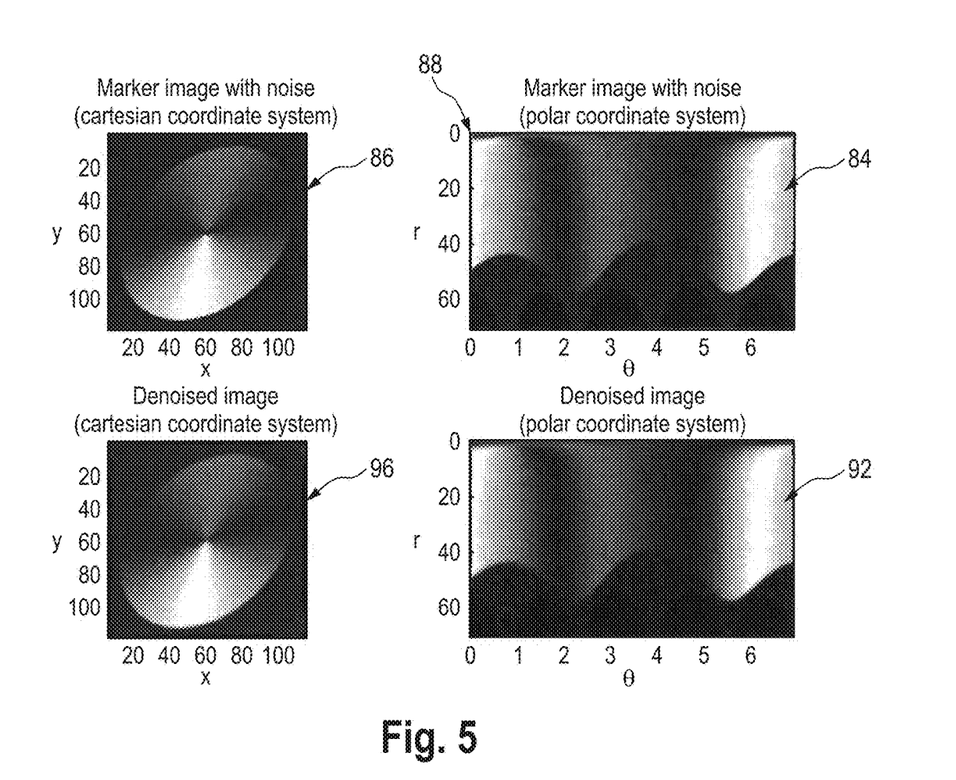
FIG. 5 shows four images for explaining an advantageous de-noising approach in accordance with some exemplary embodiments.

According to step 82 and with reference to FIG. 5, a polar coordinate image 84 is determined by means of a coordinate transformation from Cartesian coordinates to polar coordinates applied to marker image 86. Preferably, relevant ellipse center point 78 or true ellipse center point 62 is used as polar coordinate origin 88. According to step 90, a low pass filter is applied to polar coordinate image 84 for removing high frequency noise. As a result, a de-noised image 92 is obtained in the same polar coordinate system. According to step 94, the filtered polar coordinate image 92 is re-transferred into Cartesian coordinates and a corresponding de-noised Cartesian image 96 is obtained.

In a preferred embodiment, a maximum radial distance from ellipse center point 62 or, alternatively, from point of intersection 78 is defined in order to select an image area for further image analysis. The radial distance may be taken as a maximum coordinate value in the polar coordinate system. Following that, a desired resolution for the polar coordinate image may be defined and a number $N_r$ of sample values along the r-axis and a number $N_\theta$ of sample values along the θ-axis is selected. With point of intersection 78 (or ellipse center point 62) being defined as the origin of the polar coordinate system, the coordinate transformation from Cartesian coordinates to polar coordinates is carried out in accordance with:

$$x_{r,\theta} = x_0 + r \cos\theta$$

$$y_{r,\theta} = y_0 + r \sin\theta,$$

with $x_0$, $y_0$ being the coordinates of the ellipse center point 78 and with $$r = r_{max} \cdot n_r / N_r,$$

$$\theta = 2\pi \cdot n_\theta / N_\theta.$$

where $n_r = 0, 1, 2, \ldots N_{r-1}$ and $n_\theta = 0, 1, 2, \ldots N_{\theta-1}$.

In preferred embodiments, image intensity values from the original Cartesian image are interpolated in order to achieve the respective image values of the polar coordinate image 84, for example by using a bilinear interpolation algorithm. Following that, low pass filtering step 90 is carried out. Any suitable standard digital filter algorithm might be used here. Thereafter, de-noised polar coordinate image 92 is retransformed into Cartesian coordinates, wherein individual image values of de-noised Cartesian image 96 are again determined by interpolation from respective image values of image 92.

In some exemplary embodiments, original image 86 might be oversampled before the polar coordinate transformation.

According to step 98, second image values are then sampled from denoised image 96 in preferred exemplary embodiments. Preferably, the second image values are sampled along an elliptical path around point of intersection 78 and/or along an elliptical path around ellipse center point 62 in order to determine a transfer function relating marker pattern 42 to respective image pattern 100 in the elliptical representation (cf. FIG. 6).

Figure 7:
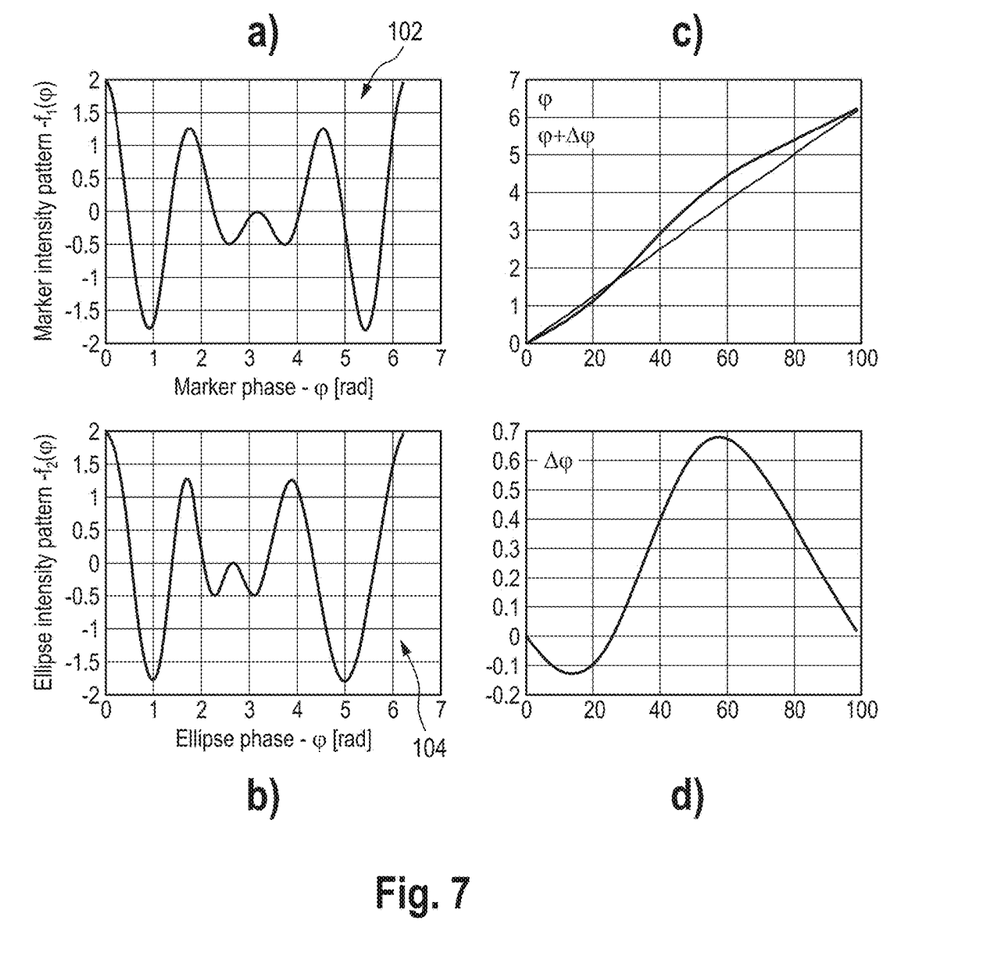
FIG. 7 shows the intensity profiles of a marker and of its elliptical representation according to FIG. 6.

By comparing sampled image pattern 100 and known marker pattern 42, it is possible to determine a transfer function that relates those two patterns. By way of example, reference is made to FIG. 7. FIG. 7*a*) shows an intensity profile 102 along a circular path around circle center point 40. FIG. 7*b*) shows the intensity profile 104 along a respective path around ellipse center point 62 or, preferably, around relevant point of intersection 78. As will be appreciated, the two intensity profiles 102, 104 are similar to each other, but not identical. In fact, intensity profile 104 is a distorted version of intensity profile 102 due to the perspective projection. Intensity profiles 102, 104 are generally related in mathematical terms as $$f_2(\varphi) = f_1(\varphi + \Delta\varphi(\varphi)),$$

with $\Delta\varphi(\varphi)$ being a non-linear function representing the distortion. In some preferred embodiments, the function $\Delta\varphi(\varphi)$ is approximated by a Fourier series $$\Delta\varphi(\varphi) = a_0 + a_1 \cos(\varphi) + a_2 \cos(2\varphi) + \ldots + a_N \cos(N\varphi) + b_1 \sin(\varphi) + \ldots + b_N \sin(N\varphi).$$

The Fourier series coefficients can be determined by solving a set of non-linear equations $$f_2(\varphi_m) - f_1(\varphi_m + \Delta\varphi(\varphi_m)) = 0$$

for m=1, 2, ..., N, with N being the number of sample values.

FIG. 7*d*) illustrates the phase difference between the intensity profiles 102, 104 resulting from the perspective projection.

Therefore, a feature transfer function is determined according to step 106 in order to establish the relationship between marker pattern 42 and image pattern 100. In some preferred embodiments, the feature transfer function is used for determining a particular correspondence between a selected marker feature and its image representation. For example, FIG. 6 shows marker pattern 42 with a characteristic feature 108 in the form of phase $\varphi_{m0}$ of radial line 110 having the highest intensity values in the marker pattern. The corresponding representation 112 in the camera image may be advantageously used for determining the correspondence between the marker feature 108 and its image representation 112.

According to step 114 further ellipse parameters, such as semi-major axis 58, semi-minor axis 60 and ellipse orientation 64 are determined. Following that, the 6-DOF-pose of marker 18 in space is determined, as is indicated in step 116, as follows: As is known to those skilled in the art, a circular contour 38 can be described in a parametrical form as $$x_m(\varphi_m) = R \cos(\varphi_m),$$

with $\varphi_m$ being a variable parameter and R being the known radius. Following that, a selected marker point on circular contour 38 can be expressed as $$x_m = R \cos(\varphi_n),$$

$$y_m = R \sin(\varphi_n).$$

Likewise, the elliptical representation can be described in parametrical form as follows:

$$x_1(\varphi_e) = R_x \cos(\varphi_e),$$

$$y_1(\varphi_e) = R_y \sin(\varphi_e),$$

$$x_e(\varphi_e) = x_1(\varphi_e)\cos(\theta) + y_1(\varphi_e)\sin(\theta) + x_0,$$

$$y_e(\varphi_e) = -x_1(\varphi_e)\sin(\theta) + y_1(\varphi_e)\cos(\theta) + y_0,$$

with $\varphi_e$ being a variable parameter and $R_x$, $R_y$, $x_0$, $y_0$ and $\theta$ being ellipse parameters that can be derived from the camera image. In particular, $R_x$ is the semi-major axis of the ellipse, $R_y$ is the semi-minor axis of the ellipse, $x_0$, $y_0$ are the coefficients of the ellipse center point, and $\theta$ is a coefficient representing ellipse orientation.

In addition to those five ellipse parameters, the correspondence between marker parameter $\varphi_{m0}$ and ellipse parameter $\varphi_{e0}$ is determined on the basis of the transfer function from step 106. The 6-DOF-pose of the marker in space can then be determined from the six ellipse parameters $R_x$, $R_y$, $x_0$, $y_0$, $\theta$, $\varphi_{e0}$.

Generally, the relationship between the 6-DOF-pose of the known marker and the ellipse parameters can be defined as $$(R_x, R_y, x_0, y_0, \theta, \varphi_{e0}) = f(t_x, t_y, t_z, \alpha, \beta, \gamma),$$

with $t_x$, $t_y$, $t_z$ being the coordinates of the marker center point in 3D space and $\alpha$, $\beta$, $\gamma$ being the rotation angles describing marker orientation in space. For a particular marker having a particular marker image pattern, a correspondence between selected points $x_m$, $y_m$ on circular marker contour 38 and respectively selected points $x_e$, $y_e$ on ellipse contour 56 are a function of the marker 6-DOF pose $$[x_e, y_e] = f(t_x, t_y, t_z, \alpha, \beta, \gamma, x_m, y_m).$$

Using the ellipse parameters derived from the camera image, it is possible to set up a system of equations relating several points $x_e$, $y_e$ on ellipse contour 56 to respective points $x_m$, $y_m$ on circular marker contour 38. There are six unknown marker parameters and two equations for each correspondence. Therefore, by establishing correspondences between three or more points $x_e$, $y_e$ on ellipse contour 56 and respective three or more points $x_m$, $y_m$ on circular marker contour 38, one can determine the 6-DOF pose of the marker by solving the set of equations. In some preferred embodiments, the set of equations is solved by using a numerical approach, such as the Levenberg-Marquardt approach. As a result, the coordinates of the marker center point in space and the rotation angles of the marker in space, i.e. its 6-DOF-pose in space, are obtained from the ellipse parameters derived from the camera image and the known marker parameters. Based on the knowledge of the 6-DOF-pose of the marker, the 6-DOF-pose of the object is then determined in step 118.

In some preferred embodiments, additional correspondences are established by relating marker circle center point 40, determined as point of intersection 78 in accordance with FIG. 4, and ellipse center point 62 as mentioned before. This helps to increase accuracy, as already mentioned before.

In summary of the above, a circular marker, as it is shown in the left-hand part of FIG. 6 by way of example, typically produces an elliptical image, as it is shown in the right-hand part of FIG. 6. Five parameters of the ellipse ($R_x$, $R_y$, $x_0$, $y_0$, $\theta$), which represent the semi-major axis, the semi-minor axis, the ellipse center point and the ellipse orientation, and a sixth parameter $\varphi_{e0}$ corresponding to a characteristic marker feature $\varphi_{m0}$ are determined from the image using image processing technologies. Once these six parameters are known, a set of non-linear equations relating the original marker in space to its image representation is established. By numerically solving the set of equations, the 6-DOF-pose of the marker in space is determined.

While preferred embodiments have been described using a parametrical description of circular marker contour and elliptical image representation, other mathematical descriptions, such as an algebraic description, might be used. In addition, various numerical algorithms might be used for solving the non-linear equations relating the original marker parameters to the elliptical image parameters. Marker pattern 42 may have different characteristics and appearances as long as it allows to find a specific correspondence between at least one characteristic marker feature and its image.

What is claimed is:

1. A method for determining a 6-DOF-pose of an object in space, said 6-DOF-pose defining a 3D-position and a 3D-orientation of the object in space, the method comprising the steps of:
   attaching a 2D optical-tracking marker to the object, said 2D optical-tracking marker comprising an inner marker area having a circular contour with a known radius and having a marker pattern defining at least one characteristic marker feature,
   providing a camera and a coordinate system relative to the camera,
   capturing an image of said 2D optical-tracking marker attached to the object by using the camera, said image comprising an elliptical representation of said circular contour as a result of a generally non-orthogonal viewing angle of said camera relative to said marker area, said elliptical representation having a semi-major axis, a semi-minor axis, an ellipse center point and an ellipse orientation relative to the coordinate system,
   based on the image, determining a first parameter representing the semi-major axis, determining a second parameter representing the semi-minor axis, determining a third parameter and a forth parameter together representing the ellipse center point, and determining a fifth parameter representing the ellipse orientation,
   identifying an image representation of said at least one characteristic marker feature in the image,
   determining a correspondence between said image representation and the at least one characteristic marker feature,
   determining a 6-DOF-pose of the 2D optical-tracking marker in space based on the first parameter, the second parameter, the third parameter, the fourth parameter, the fifth parameter and the correspondence, and
   determining the 6-DOF-pose of the object based on the 6-DOF-pose of the 2D optical-tracking marker.

2. The method of claim 1, wherein the circular contour defines a circle center point, and wherein the marker pattern comprises an intensity profile that varies substantially continuously along a circular path around the circle center point.

3. The method of claim 2, wherein the intensity profile is constant along any radial path starting at the circle center point and extending radially outward from the circle center point a defined distance.

4. The method of claim 1, further comprising:
   a step of sampling a plurality of first image values in the image,
   a step of determining a plurality of gradient vectors, each gradient vector representing a direction of maximum change in the intensity profile at a respective first image value, and
   a step of determining a marker center point based on the plurality of gradient vectors.

5. The method of claim 1, wherein the circular contour defines a circle center point, and wherein the marker pattern comprises intensity values that vary in accordance with a function that results from a linear combination of a limited number of sinusoidal components along a circular path around the circle center point.

6. The method of claim 1, wherein the marker pattern is a greyscale pattern.

7. The method of claim 1, wherein the marker pattern comprises at least three different color components.

8. The method of claim 1, wherein the marker pattern is radially-symmetric.

9. The method of claim 1, wherein the circular contour defines a circle center point, and wherein the characteristic feature comprises a rotation angle of the marker pattern around the circle center point.

10. The method of claim 1, further comprising a step of sampling a plurality of second image values in the image along an elliptical path around the ellipse center point in order to determine an image pattern, and comprising a step of determining a transfer function representing a relationship between the marker pattern and the image pattern.

11. The method of claim 10, wherein the transfer function is determined using a Fourier series.

12. The method of claim 1, further comprising the steps of:
   determining a polar coordinate image from the image by means of a coordinate transformation from Cartesian coordinates to polar coordinates using the ellipse center point as a polar coordinate origin, low pass filtering of the polar coordinate image in order to determine a de-noised polar coordinate image, and determining a de-noised Cartesian coordinate image from the de-noised polar coordinate image by means of a coordinate transformation from polar coordinates to Cartesian coordinates.

13. The method of claim 1, wherein the step of determining the 6-DOF-pose of the 2D optical-tracking marker comprises a step of numerically solving a system of equations relating the 6-DOF-pose of the 2D optical-tracking marker in space to the first parameter, the second parameter, the third parameter, the fourth parameter, the fifth parameter and the correspondence.

14. The method of claim 1, wherein precisely one 2D optical-tracking marker is attached to the object and one image of said 2D optical-tracking marker is used in the step of determining the first parameter, the second parameter, the third parameter, the fourth parameter, the fifth parameter and the correspondence.

15. The method of claim 1, wherein a plurality of 2D optical-tracking markers are attached to the object.

16. The method of claim 15, wherein the plurality of 2D optical-tracking markers comprise a first 2D optical-tracking marker having a first marker pattern and comprise a second 2D optical-tracking marker having a second marker pattern, the first and second marker patterns being different from one another.

17. The method of claim 1, wherein the 2D optical-tracking marker further comprises an outer background area that distinguishes from the inner marker area.

18. A system for determining a 6-DOF-pose of an object in space, said 6-DOF-pose defining a 3D-position and a 3D-orientation of the object in space, the system comprising:
 a 2D optical-tracking marker configured to be attached to the object, said 2D optical-tracking marker comprising an inner marker area having a circular contour with a known radius and having a marker pattern defining at least one characteristic marker feature,
 a camera, and
 a processing unit configured for executing steps of:
 defining a coordinate system relative to the camera,
 capturing an image of said 2D optical-tracking marker attached to the object by using the camera, said image comprising an elliptical representation of said circular contour as a result of a generally non-orthogonal viewing angle of said camera relative to said marker area, said elliptical representation having a semi-major axis, a semi-minor axis, an ellipse center point and an ellipse orientation relative to the coordinate system,
 based on the image, determining a first parameter representing the semi-major axis, determining a second parameter representing the semi-minor axis, determining a third parameter and a forth parameter together representing the ellipse center point, and determining a fifth parameter representing the ellipse orientation,
 identifying an image representation of said at least one characteristic marker feature in the image,
 determining a correspondence between said image representation and the at least one characteristic marker feature,
 determining a 6-DOF-pose of the 2D optical-tracking marker in space based on the first parameter, the second parameter, the third parameter, the fourth parameter, the fifth parameter and the correspondence, and
 determining the 6-DOF-pose of the object based on the 6-DOF-pose of the 2D optical-tracking marker.

19. A computer program product comprising a non-transitory data carrier for storing program code designed for determining a 6-DOF-pose of an object in space, said 6-DOF-pose defining a 3D-position and a 3D-orientation of the object in space, said program code being configured for performing the following steps when executed on a processing unit connected to a camera:
 defining a coordinate system relative to the camera,
 capturing an image of said 2D optical-tracking marker attached to the object by using the camera, said image comprising an elliptical representation of said circular contour as a result of a generally non-orthogonal viewing angle of said camera relative to said marker area, said elliptical representation having a semi-major axis, a semi-minor axis, an ellipse center point and an ellipse orientation relative to the coordinate system,
 based on the image, determining a first parameter representing the semi-major axis, determining a second parameter representing the semi-minor axis, determining a third parameter and a forth parameter together representing the ellipse center point, and determining a fifth parameter representing the ellipse orientation,
 identifying an image representation of said at least one characteristic marker feature in the image,
 determining a correspondence between said image representation and the at least one characteristic marker feature,
 determining a 6-DOF-pose of the 2D optical-tracking marker in space based on the first parameter, the second parameter, the third parameter, the fourth parameter, the fifth parameter and the correspondence, and
 determining the 6-DOF-pose of the object based on the 6-DOF-pose of the 2D optical-tracking marker.

\* \* \* \* \*